US005688986A

United States Patent [19]

Tam et al.

[11] Patent Number: 5,688,986

[45] Date of Patent: Nov. 18, 1997

[54] PROCESSES AND CATALYST COMPOSITIONS FOR HYDROCYANATION OF MONOOLEFINS

[75] Inventors: Wilson Tam, Boothwyn, Pa.; Kristina Ann Kreutzer; Ronald James McKinney, both of Wilmington, Del.

[73] Assignee: E. I. Du Pont de Nemours and Company, Wilmington, Del.

[21] Appl. No.: 424,351

[22] PCT Filed: Nov. 7, 1994

[86] PCT No.: PCT/US94/12794

§ 371 Date: Apr. 26, 1995

§ 102(e) Date: Apr. 26, 1995

[87] PCT Pub. No.: WO95/14659

PCT Pub. Date: Jun. 1, 1995

Related U.S. Application Data

[63] Continuation-in-part of Ser. No. 198,963, Feb. 18, 1994, abandoned, which is a continuation-in-part of Ser. No. 157,342, Nov. 23, 1993, abandoned.

[51] Int. Cl.[6] .......... C07C 253/30

[52] U.S. Cl. .......... 558/338; 558/337

[58] Field of Search .......... 558/78, 338, 337; 568/12; 556/13

[56] References Cited

U.S. PATENT DOCUMENTS

| | | | |
|---|---|---|---|
| 3,496,210 | 2/1970 | Drinkard, Jr. et al. | 260/465 |
| 3,496,215 | 2/1970 | Drinkard, Jr. et al. | 260/465.8 |
| 3,496,217 | 2/1970 | Drinkard, Jr. et al. | 260/465 |
| 3,496,218 | 2/1970 | Drinkard, Jr. | 260/465.8 |
| 3,536,748 | 10/1970 | Drinkard, Jr. et al. | 260/465.9 |
| 3,547,942 | 12/1970 | Godefroi et al. | 260/309 |
| 3,574,701 | 4/1971 | Kominami et al. | 260/465.3 |
| 3,578,695 | 5/1971 | Milberger et al. | 260/465.3 |
| 3,584,029 | 6/1971 | Kominami et al. | 260/465.3 |
| 3,631,191 | 12/1971 | Kane et al. | 260/439 |
| 3,655,723 | 4/1972 | Drinkard, Jr. | 260/465.3 |
| 3,676,481 | 7/1972 | Chia | 260/465.9 |
| 3,739,011 | 6/1973 | Drinkard, Jr. | 558/355 |
| 3,766,231 | 10/1973 | Gosser et al. | 260/439 R |
| 3,766,237 | 10/1973 | Chia et al. | 260/465.3 |
| 3,773,809 | 11/1973 | Walter | 260/465.8 |
| 3,775,461 | 11/1973 | Drinkard et al. | 260/465.3 |
| 3,798,256 | 3/1974 | King et al. | 558/338 |
| 3,846,461 | 11/1974 | Shook, Jr. | 260/439 R |
| 3,847,959 | 11/1974 | Shook, Jr. et al. | 260/439 R |
| 3,852,325 | 12/1974 | King | 558/355 |
| 3,852,328 | 12/1974 | Chia et al. | 558/355 |
| 3,852,329 | 12/1974 | Tomlinson | 558/355 |
| 3,853,948 | 12/1974 | Drinkard, Jr. et al. | 558/355 |
| 3,865,864 | 2/1975 | Nakajima et al. | 26/465.3 |
| 3,869,500 | 3/1975 | Kominami et al. | 260/465.3 |
| 3,903,120 | 9/1975 | Shook, Jr. et al. | 260/439 R |
| 3,925,445 | 12/1975 | King et al. | 558/338 |
| 4,298,546 | 11/1981 | McGill | 558/355 |
| 4,371,474 | 2/1983 | Rapoport | 558/338 |
| 4,599,206 | 7/1986 | Billig et al. | 558/85 |
| 4,668,651 | 5/1987 | Billig et al. | 502/158 |
| 4,688,651 | 8/1987 | Dysart | 175/371 |
| 4,705,881 | 11/1987 | Rapoport | 558/338 |
| 4,714,773 | 12/1987 | Rapoport | 558/338 |
| 4,717,775 | 1/1988 | Billig et al. | 568/454 |
| 4,769,498 | 9/1988 | Billig et al. | 568/454 |
| 4,774,353 | 9/1988 | Hall et al. | 558/335 |
| 4,783,546 | 11/1988 | Burke et al. | 558/355 |
| 4,810,815 | 3/1989 | Bryndza | 558/338 |
| 4,874,884 | 10/1989 | McKinney et al. | 558/338 |
| 5,202,297 | 4/1993 | Lorz et al. | 502/106 |
| 5,235,113 | 8/1993 | Sato et al. | 568/454 |
| 5,312,957 | 5/1994 | Casalnuovo et al. | 558/410 |
| 5,312,996 | 5/1994 | Packett | 568/454 |
| 5,360,938 | 11/1994 | Babin et al. | 568/449 |
| 5,364,950 | 11/1994 | Babin et al. | 556/2 |
| 5,440,067 | 8/1995 | Druliner | 558/355 |
| 5,491,266 | 2/1996 | Babin et al. | 568/449 |
| 5,512,695 | 4/1996 | Kreutzer et al. | 558/338 |

FOREIGN PATENT DOCUMENTS

| | | | |
|---|---|---|---|
| 0 518 241 | 12/1992 | European Pat. Off. | C07C 45/50 |
| 6916495 | 5/1971 | Netherlands | C07C 121/00 |
| 1 417 554 | 12/1975 | United Kingdom | C07F 9/02 |
| WO 85/03702 | 8/1985 | WIPO | C07C 45/50 |
| WO 93/03839 | 3/1993 | WIPO | B01J 31/24 |

OTHER PUBLICATIONS

Cuny, G.D. et al, "Practical, High–Yield, Regioselective, Rhodium–Catalyzed Hydroformylation of Functionalized α–Olefins", *J. Am. Chem. Soc.*, 115, 2066–2068 (1993).

Burgstahler, A.W. et al, "Improved Modification of the Rosenmund Reduction", *Synthesis*, 767–768 (1976).

Tolman, C.A. et al, "Homogeneous Nickel–Catalyzed Olefin Hydrocyanation", *Advances in Catalysis*, 33 (1985).

Baker, M.J. et al, "Chelating Diphosphite Complexes of Nickel(0) and Platinum(0): Their Remarkable Stability and Hydrocyanation Activity", *J. Chem. Soc., Chem. Commun.*, pp. 803–804 (1991).

Baker, M.J. et al, "Chiral Aryl Diphosphites: A New Class of Ligands for Hydrocyanation Catalysis", *J. Chem. Soc., Chem. Communi.*, 1292–1293 (1991).

Seidel, W.C. et al, "Ethylene[bis(tri–o–tolyl phosphite)] nickel(0)", *Inorganic Chemistry*, 9(10), 2354–2357 (1970).

Kurokawa, H. et al, "Skeletal Rearrangement of Unsaturated Nitriles over Solid–Base Catalysts", *J. of Catalysis*, 141, 94–101 (1993).

Pastor, S.D. et al, "Conformation of Eight–Membered Dioxathiasilocin Heterocycles in Solution", *Phosphorus and Sulfur*, 32, 105–111 (1987).

Yamada, F. et al, "Substituted Bisphenols as Antioxidants for Autoxidation of Tetralin", *Bull. Chem. Soc. Japan*, 62, 3603–3608 (1989).

*Primary Examiner*—Johann Richter
*Assistant Examiner*—Laura R. Cross

[57] ABSTRACT

Processes for hydrocyanation of nonconjugated acyclic aliphatic monoolefins, monoolefins conjugated to an ester group, or monoolefins conjugated to a nitrile group which utilize a catalyst precursor composition comprising a bidentate phosphite ligand and zero-valent nickel preferably in the presence of a Lewis acid prompter. Catalyst precursor compositions are also disclosed.

18 Claims, No Drawings

PROCESSES AND CATALYST COMPOSITIONS FOR HYDROCYANATION OF MONOOLEFINS

CROSS-REFERENCE TO RELATED APPLICATIONS

This application claims priority benefit under 35 U.S.C. 371 from PCT/US94/12794 filed Nov. 7, 1994, which is, in-turn, a continuation-in-part application of application Ser. No. 08/198,963 filed Feb. 18, 1994, now abandoned, which is, in-turn, a continuation-in-part application of application Ser. No. 08/157,342 filed Nov. 23, 1993, now abandoned.

FIELD OF THE INVENTION

This invention relates to processes and catalyst compositions useful in the hydrocyanation of monoolefins. In particular, the invention relates to the hydrocyanation of monoolefins using zero-valent nickel and a bidentate phosphite ligand in the presence of a Lewis acid promoter.

BACKGROUND OF THE INVENTION

Hydrocyanation catalyst systems, particularly pertaining to the hydrocyanation of olefins, are known in the art. For example, systems useful for the hydrocyanation of butadiene to form pentenenitrile and in the subsequent hydrocyanation of pentenenitrile (PN) to form adiponitrile (ADN), are known in the commercially important nylon synthesis field. The hydrocyanation of olefins using transition metal complexes with monodentate phosphite ligand is documented in the prior art. See for example; U.S. Pat. Nos. 3,496,215, 3,631,191, 3,655,723 and 3,766,237, and Tolman, C. A.; McKinney, R. J.; Seidel, W. C.; Druliner, J. D.; and Stevens, W. R.; Advances in Catalysis, 33, 1, 1985.

The hydrocyanation of activated olefins such as with conjugated olefins (e.g., butadiene and styrene) and strained olefins (e.g., norbornene) proceeds without the use of a Lewis acid promoter, while hydrocyanation of unactivated olefins such as 1-octene and 3-pentenenitrile requires the use of a Lewis acid promoter. Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters.

U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including PN, in the presence of a zero-valent nickel catalyst and a triorganotin catalyst promoter. U.S. Pat. No. 4,874,884 discloses a process for producing ADN by the zero-valent nickel catalyzed hydrocyanation of pentenenitriles in the presence of a synergistic combination of promoters selected in accordance with the reaction kinetics of the ADN synthesis.

Bidentate phosphite ligands similar to those used in the present invention for the hydrocyanation of monoolefins have been shown to be useful ligands in the hydrocyanation of activated olefins. See, for example: Baker, M. J., and Pringle, P. G.; J. Chem. Soc., Chem. Commun., 1292, 1991; Baker, M. J.; Harrison, K. N.; Orpen, A. G.; Pringle, P. G.; and Shaw, G.; J. Chem. Soc.; Chem. Commun., 803, 1991, Union Carbide, WO 93,03839.

Also, some of the ligands of the present invention have been disclosed with rhodium in catalyst complexes useful for the hydroformylation of functionalized olefins; see, Cuny, G. D., Buchwald, S. L., J. Am. Chem. Soc. 1993, 115, 2066.

The present invention provides for novel processes and catalyst precursor compositions which are more rapid, selective, efficient and stable than current processes and catalyst complexes employed in the hydrocyanation of monoolefins. Other objects and advantages of the present invention will become apparent to those skilled in the art upon reference to the detailed description of the invention which hereinafter follows.

SUMMARY OF THE INVENTION

The present invention provides a process for hydrocyanation comprising reacting a nonconjugated acyclic aliphatic monoolefin, a monoolefin conjugated to an ester group, e.g., methyl pent-2-eneoate, or a monoolefin conjugated to a nitrile group, e.g., 3-pentenenitrile; with a source of HCN in the presence of a catalyst precursor composition comprising zero-valent nickel and a bidentate phosphite ligand of Formula I,

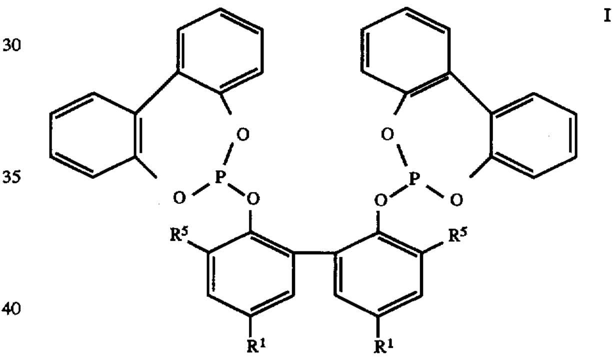

wherein each $R^1$ is independently a tertiary substituted hydrocarbon of up to 12 carbon atoms, or $OR^4$ wherein $R^4$ is $C_1$ to $C_{12}$ alkyl;

each $R^5$ is independently a tertiary substituted hydrocarbon of up to 12 carbon atoms;

and wherein said reaction is carried out to produce a terminal organonitrile. Preferably, the reaction is carried out in the presence of a Lewis acid promoter.

The present invention further provides a process for hydrocyanation comprising reacting a nonconjugated acyclic aliphatic monoolefin, a monoolefin conjugated to an ester group, e.g., methyl pent-2-eneoate, or a monoolefin conjugated to a nitrile group, e.g., 3-pentene-nitrile; with a source of HCN in the presence of a catalyst precursor composition comprising zero-valent nickel and a bidentate phosphite ligand of Formulas II, III, IV, or V, as set forth below, and wherein said reaction is carried out to produce a terminal organonitrile. Preferably, the reaction is carried out in the presence of a Lewis acid promoter.

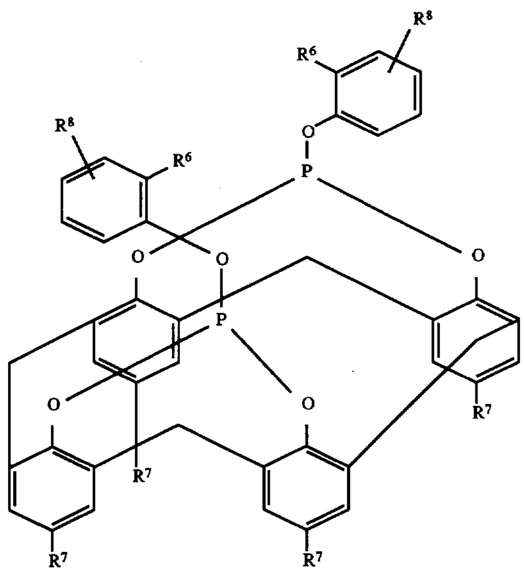

wherein each $R^6$ and $R^7$ is independently a tertiary substituted hydrocarbon of up to 12 carbon atoms; and each $R^8$ is independently H or a branched or straight chain alkyl of up to 12 carbon atoms, or $OR^4$ wherein $R^4$ is $C_1$ to $C_{12}$ alkyl.

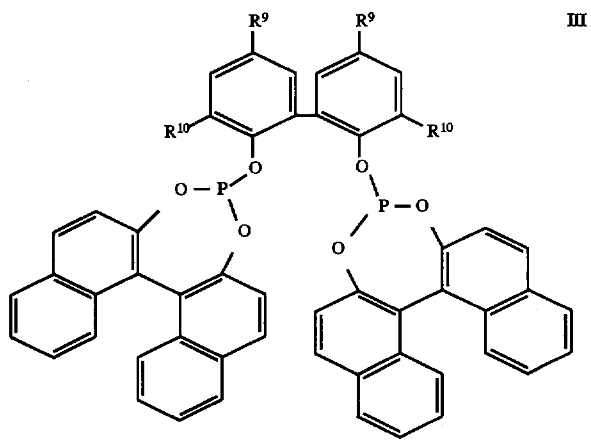

wherein each $R^9$ is independently H or a branched or straight chain alkyl of up to 12 carbon atoms, or $OR^4$ wherein $R^4$ is $C_1$ to $C_{12}$ alkyl; and each $R^{10}$ is independently a tertiary substituted hydrocarbon of up to 12 carbon atoms.

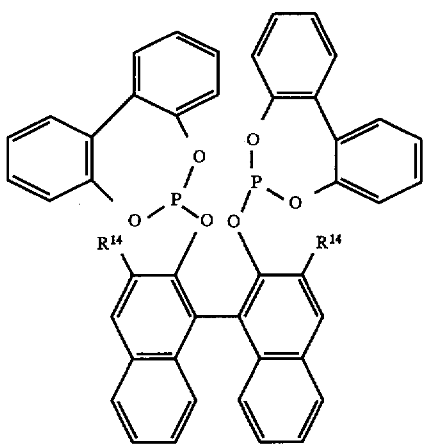

wherein each $R^{14}$ is independently a tertiary substituted hydrocarbon of up to 12 carbon atoms or $Si(R^{11})_3$ where $R^{11}$ is independently a branched or straight chain alkyl of up to 12 carbon atoms or phenyl.

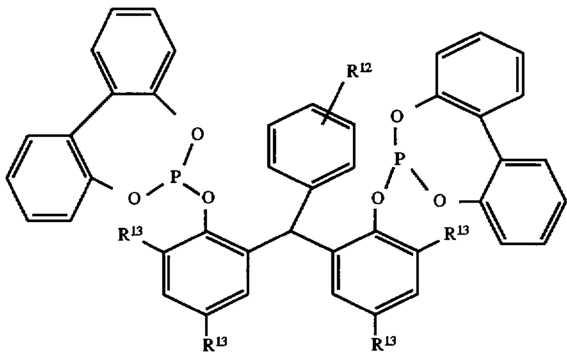

wherein $R^{12}$ is H or a branched or straight chain alkyl of up to 12 carbon atoms; and each $R^{13}$ is independently a branched or straight chain alkyl of up to 12 carbon atoms.

The monoolefins of the above-identified processes are described by Formulas VI or VIII, and the corresponding terminal organonitrile compounds produced are described by Formulas VII or IX, respectively.

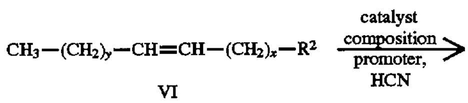

$$CH_3-(CH_2)_y-CH=CH-(CH_2)_x-R^2 \xrightarrow[\text{promoter, HCN}]{\text{catalyst composition}} NC-(CH_2)_{y+x+3}-R^2$$

VI VII wherein $R^2$ is H, CN, $CO_2R^3$, or perfluoroalkyl;

y is 0 to 12;

x is 0 to 12; and $R^3$ is alkyl; or $$CH_2{=}CH{-}(CH_2)_x{-}R^2 \xrightarrow[\text{promoter, HCN}]{\text{catalyst composition}} NC{-}(CH_2)_{x+2}{-}R^2$$

VIII → IX wherein $R^2$ is H, CN, $CO_2R^3$, or perfluoroalkyl;

x is 0 to 12; and $R^3$ is alkyl.

The present invention also provides for a catalyst precursor composition comprising zero-valent nickel and a bidentate phosphite ligand of Formula I,

I

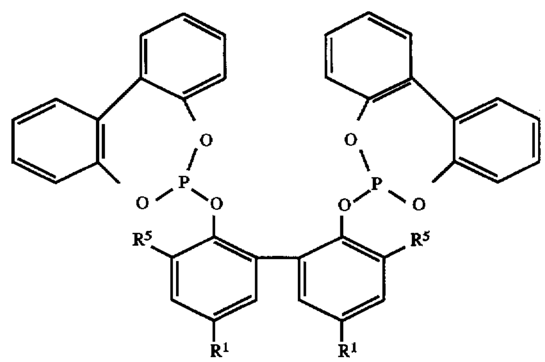

wherein each $R^1$ is independently a tertiary substituted hydrocarbon of up to 12 carbon atoms, or $OR^4$ wherein $R^4$ is $C_1$ to $C_{12}$ alkyl; and each $R^5$ is independently a tertiary substituted hydrocarbon of up to 12 carbon atoms.

The present invention further provides for catalyst precursor compositions comprising zero-valent nickel and a bidentate phosphite ligand of Formulas II, III, IV, or V, set forth below.

II

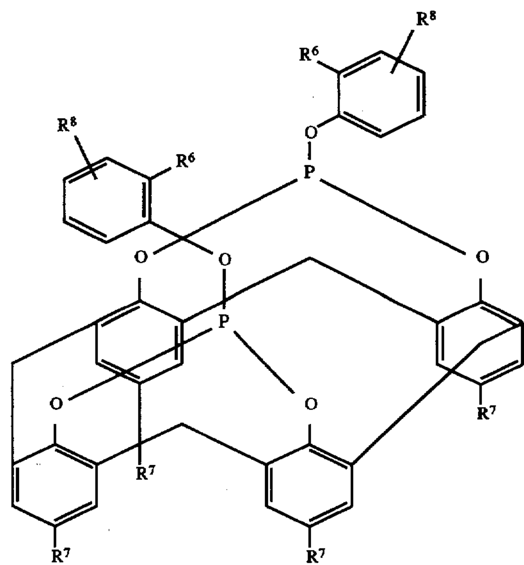

wherein each $R^6$ and $R^7$ is independently a tertiary substituted hydrocarbon of up to 12 carbon atoms; and each $R^8$ is independently H or a branched or straight chain alkyl of up to 12 carbon atoms, or $OR^4$ wherein $R^4$ is $C_1$ to $C_{12}$ alkyl.

III

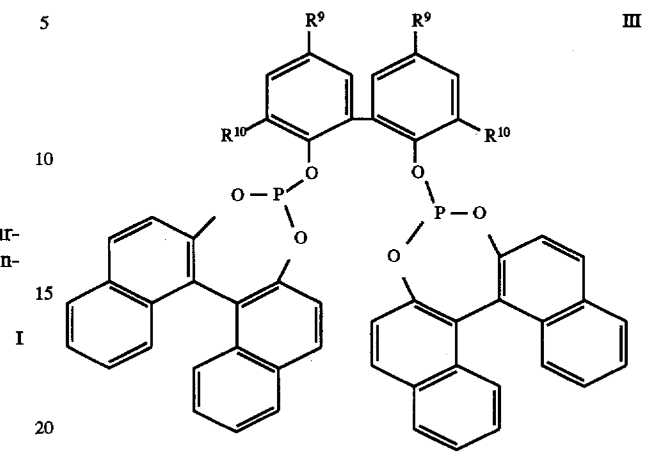

wherein each $R^9$ is independently H or a branched or straight chain alkyl of up to 12 carbon atoms, or $OR^4$ wherein $R^4$ is $C_1$ to $C_{12}$ alkyl; and each $R^{10}$ is independently a tertiary substituted hydrocarbon of up to 12 carbon atoms.

IV

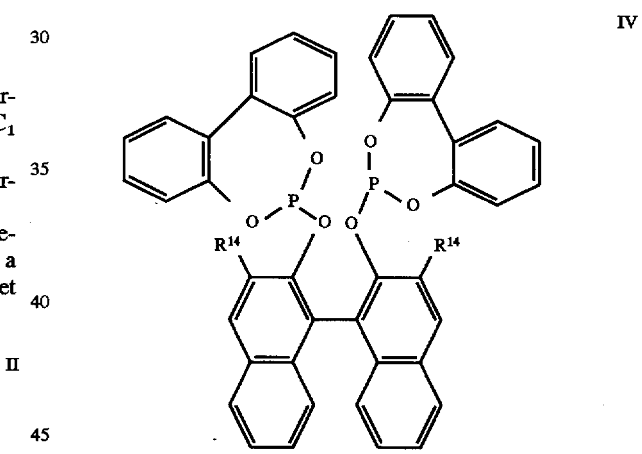

wherein each $R^{14}$ is independently a tertiary substituted hydrocarbon of up to 12 carbon atoms or $Si(R^{11})_3$ where $R^{11}$ is independently a branched or straight chain alkyl of up to 12 carbon atoms or phenyl.

V

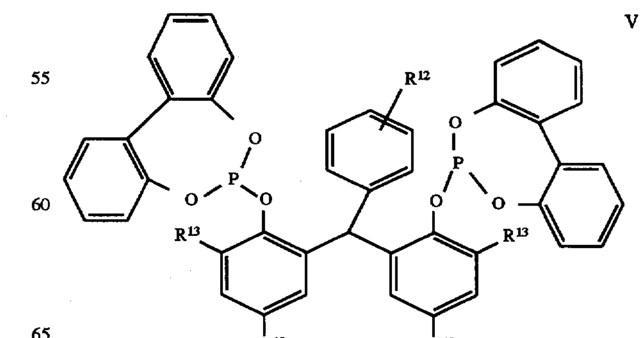

wherein $R^{12}$ is H or a branched or straight chain alkyl of up to 12 carbon atoms; and each $R^{13}$ is independently a branched or straight chain alkyl of up to 12 carbon atoms.

Preferably, the catalyst precursor compositions of Formulas I, II, III, IV and V further comprise a Lewis acid promoter.

DETAILED DESCRIPTION OF THE PREFERRED EMBODIMENTS

The catalyst precursor compositions of the invention are comprised of a bidentate phosphite ligand and zero-valent nickel. The preferred ligand of the invention is described below by Formula I, wherein each $R^1$ is independently a tertiary substituted hydrocarbon containing up to 12 carbon atoms, or $OR^4$ wherein $R^4$ is a $C_1$ to $C_{12}$ alkyl. $R^4$ can be primary, secondary or tertiary; examples include methyl, ethyl, isopropyl and t-butyl. Each $R^1$ may be the same or different. In a more preferred ligand both $R^1$ groups are $OR^4$ wherein $R^4$ is methyl. $R^5$ is a tertiary substituted hydrocarbyl group containing up to 12 single bond carbon atoms.

Applicants have referred to the catalyst composition of the invention as a "precursor" composition only to indicate that in all likelihood, during the hydrocyanation reaction the structure of the active catalyst composition may in fact be complexed to an olefin.

I

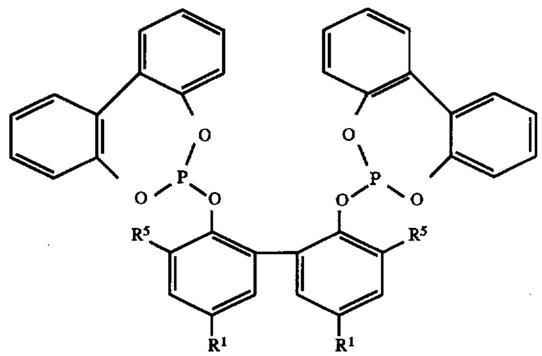

These ligands may be prepared by a variety of methods known in the art, for example see descriptions in WO 93,03839, U.S. Pat. No. 4,769,498; U.S. Pat. No. 4,688,651, J. Amer. Chem. Soc., 115 , 2066, 1993. The reaction of 2,2'-biphenol with phosphorus trichloride gives 1,1'-biphenyl-2,2'-diyl phosphorochloridite. The reaction of this chloridite with 2,2'-dihydroxy-3,3'-di-t-butyl-5,5'-dimethoxy-1,1'-biphenyl in the presence of triethylamine gives the most preferred ligand wherein $R^1$ is methoxyl.

Other bidentate phosphite ligands of the invention are described above by Formulas II, III, IV, and V. While these ligands are not as preferred as Formula I, they nevertheless are considered useful ligands of the present invention. These ligands may be prepared according to the non-limiting examples set forth below.

The zero-valent nickel can be prepared or generated according to techniques known in the art (U.S. Pat. Nos. 3,496,217; 3,631,191; 3,846,461; 3,847,959; and 3,903,120 which are incorporated herein by reference). Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni(P(O\text{-}o\text{-}C_6H_4CH_3)_3)_2(C_2H_4)$, both of which are known in the art. Alternatively, divalent nickel compounds may be combined with a reducing agent, and are then able to serve as suitable sources of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated cataylst, as described in U.S. Pat. No. 3,903,120, is also a suitable source of zero-valent nickel.

The nonconjugated acyclic aliphatic monoolefin substrates of the invention include unsaturated organic compounds containing from 2 to approximately 30 carbon atoms having at least one nonconjugated aliphatic carbon-carbon double bond. The 3-pentenenitriles and 4-pentenenitriles are especially preferred. Suitable unsaturated compounds include olefins and olefins substituted with groups which do not attack the catalyst, such as cyano. These unsaturated compounds include monoolefins containing from 2 to 30 carbons such as ethylene, propylene, butene-1, pentene-2, hexene-2, etc., nonconjugated diolefins such as allene, and substituted compounds such as 2-pentenenitriles, 3-pentenenitriles, 4-pentenenitriles and methyl pent-3-enoate. The monoolefins may also be conjugated to an ester group or a nitrile group such as methyl pent-2-enoate and 2-pentenenitrile, respectively.

Two formulas are presented below which together describe these substrates of the invention; Formulas VI and VIII. Substrates of Formula VI yield terminal organonitriles of Formula VII, while Formula VIII substrates will yield terminal organonitriles of Formula IX.

$$CH_3\text{—}(CH_2)_y\text{—}CH\text{=}CH\text{—}(CH_2)_xR^2 \qquad \text{VI}$$

wherein $R^2$ is H, CN, $CO_2R^3$, or perfluoroalkyl;

y is 0 to 12;

x is 0 to 12; and $R^3$ is alkyl;

produces the terminal organonitrile product compound of Formula VI $$NC\text{—}(CH_2)_{y+x+3}\text{—}R^2 \qquad \text{VII}$$

wherein $R^2$, y and x are as defined above.

$$CH_2\text{=}CH\text{—}(CH_2)_xR^2 \qquad \text{VIII}$$

wherein $R^2$ is H, CN, $CO_2R^3$, or perfluoroalkyl;

x is 0 to 12; and $R^3$ is alkyl, produces the terminal organonitrile product compound of Formula IX $$NC\text{—}(CH_2)_{x+2}\text{—}R^2 \qquad \text{IX}$$

wherein $R^2$ and x are as defined above.

Perfluoroalkyl is defined as $C_z(F_{2z+1})$ where z is 1 to 12.

Preferred substrates are nonconjugated linear alkenes, nonconjugated linear alkenenitriles, nonconjugated linear alkenoates, linear alk-2-enoates and perfluoroalkyl ethylenes. Most preferred substrates include 2-, 3- and 4-pentenenitrile, alkyl 2- and 3- and 4-penteneoates, and $C_xF_{2x+1}CH{=}CH_2$ (where x is 1 to 12).

The preferred products are terminal alkanenitriles, linear alkanedinitriles, linear alkane(nitrile)esters, and 3-(perfluoroalkyl)propionitrile. Most preferred products are adiponitrile, alkyl 5-cyanovalerate, and $C_xF_{2x+1}CH_2CH_2CN$ (where x is 1 to 12).

The present hydrocyanation processes may be carried out by charging a reactor with all of the reactants, or preferably the reactor is charged with the catalyst precursor composition or catalyst components, the unsaturated organic compound, the optionally present promoter and the solvent to be used and the hydrogen cyanide added slowly. HCN may be delivered as a liquid or as a vapor to the reaction. Another technique is to charge the reactor with the catalyst, optionally present promoter, and the solvent to be used, and feed both the unsaturated compound and the HCN slowly to the reaction mixture. The molar ratio of unsaturated compound to catalyst generally is varied from about 10:1 to 2000:1.

Preferably, the reaction medium is agitated, such as by stirring or shaking. The cyanated product can be recovered by conventional techniques such as distillation. The reaction may be run either batchwise or in a continuous manner.

The hydrocyanation reaction can be carried out with or without a solvent. The solvent should be liquid at the reaction temperature and pressure and inert towards the unsaturated compound and the catalyst composition. Generally, such solvents are hydrocarbons such as benzene or xylene, or nitriles such as acetonitrile or benzonitrile. In some cases, the unsaturated compound to be hydrocyanated may serve as the solvent.

The exact temperature which is preferred is dependent to a certain extent on the particular catalyst composition being used, the particular unsaturated compound being used and the desired rate. Generally, temperatures of from about −25° to about 200° C. can be used, with from about 0° to about 150° C. being preferred.

Atmospheric pressure is satisfactory for carrying out the present invention and hence pressures of from about 0.05 to about 10 atmospheres are preferred due to obvious economic considerations. However, pressures of from about 0.05 to about 100 atmospheres can be used if desired.

HCN may be added to the reaction as vapor or liquid, or in a system utilizing a cyanohydrin as the carrier. See, for example, U.S. Pat. No. 3,655,723 the contents of which are incorporated herein by reference.

The processes of this invention can be and preferably are carried out in the presence of one or more Lewis acid promoters which affect both the activity and selectivity of the catalyst system. The promoter may be an inorganic or organometallic compound in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Suitable promoters are further described in U.S. Pat. Nos. 3,496,217; 3,496,218; and 4,774,353, the contents of which are incorporated herein by reference. These include metal salts (such as $ZnCl_2$, $CoI_2$, and $SnCl_2$) and organometallic compounds (such as $RAlCl_2$, $R_3SnO_3SCF_3$, and $R_3B$, where R is an alkyl or aryl group).

U.S. Pat. No. 4,874,884 describes how synergistic combinations of promoters may be chosen to increase the catalytic activity of the catalyst system. Preferred promoters are $CdCl_2$, $ZnCl_2$, $B(C_6H_5)_3$, and $(C_6H_5)_3SnX$, where $X{=}CF_3SO_3$, $CH_3C_6H_5SO_3$, or $(C_6H_5)_3BCN$. The amount of promoter to nickel to promoter present in the reaction may be in the range of from about 1:16 to about 50:1.

EXAMPLES

The following non-limiting examples further embody and enable the processes and catalyst compositions of the invention. Generally, HCN reactions were done using the following procedure unless otherwise noted. The mixtures were heated in a thermostatically controlled oil bath. HCN was delivered to the flask as an $HCN/N_2$ gas mixture by bubbling dry nitrogen gas through liquid HCN at 0° C. (maintained in an ice bath); this provides a vapor stream which is about 35% HCN (vol/vol). The rate of nitrogen gas flow determines the rate of HCN delivery. Sample analysis was carried out by gas chromatographic (GC) analysis. The ligand, unless otherwise noted, was {2,2'-bis[1,1'-biphenyl-2,2'-diyl)phosphite]-3,3'-di-t-butyl-5,5'dimethoxy-1,1'-biphenyl} (Ligand "A").

EXAMPLE 1

Preparation of the Ligand of Formula I (Ligand "A")

Ligand "A" (corresponding to Formula I) may be prepared using a literature procedure, for example see descriptions in WO 93,03839, U.S. Pat. No. 4,769,498; U.S. Pat. No. 4,688,651, J. Amer. Chem. Soc., 115, 2066, 1993.

A solution of 2,2'-biphenol (28.1 g, 0.151 mol) in 49 mL phosphorus trichloride was heated at reflux for 2 hr. The excess PCl3 was removed by distillation. The residue was purified by vacuum distillation (140°–143° C. at 0.5 mm Hg) to give 30.70 g (81% yield) 1,1'-biphenyl-2,2'-diyl phosphorochloridite (as a clear viscous oil which solidified to a white solid upon standing at room temperature (RT) in an inert atmosphere for an extended period of time). $^{31}P\{^1H\}$NMR (121.4 MHz, $d_8$-toluene): δ 180.1 (s), 85% $H_3PO_4$ external reference.

Then to a solution of 1,1'-biphenyl-2,2'-diyl phosphorochloridite (1.40 g, 5.6 mmol) in 0.6 mL toluene at −40° C. was added, over a 15 min period, a solution of 2,2'-dihydroxy-3,3'-di-t-butyl-5,5'-dimethoxy-1,1'-biphenyl (1.00 g, 2.80 mmol) and triethylamine (1.79 mL, 22.4 mmol) in 12 mL toluene. The resulting mixture was allowed to warm slowly (overnight) to room temperature. After the addition of water (6.5 mL), the reaction mixture was filtered. The residue was washed several times with water and dried in vacuo overnight to give a white solid. The solid was recrystallized from acetonitrile to give a white powder (0.72 g, 33% yield). $^1H$ NMR (300 MHz, $CDCl_3$): δ 1.46 (s, 18H); 3.39 (s, 6H); 6.90–7.32 (m, 20H); $^{31}P\{^1H\}$NMR (121.4 MHz, $d_8$-$CDCl_3$): δ 147.0 (s), 85% $H_3PO_4$ external reference.

EXAMPLE 2

Hydrocyanation of 3-Pentenenitrile with ligand/Ni $(COD)_2$(bis (1,5-cyclooctadiene)nickel): $ZnCl_2$ Promoter 350 mg of Ligand "A" (0.44 mmoles) and 20 mg of $Ni(COD)_2$ (0.073 mmoles) were dissolved in 5 mL of tetrahydrofuran (THF). The solvent was removed by vacuum evaporation. 5 mL of 3PN and 10 mg (0.073 mmoles) of $ZnCl_2$ were added. The mixture was treated with HCN at 30 cc/min of $N_2$ at 50° C. for 15 minutes, 60° C. for 15 minutes, and 70° C. for 15 minutes. After this time; GC analysis indicated area % of 77.1% ADN and 20.7% 2-methyl-glutaronitrile (MGN).

The above procedure was repeated using 85 mg (0.11 mmoles) of Ligand "A". After heating at 70° C.; G.C. analysis indicated area % of 45.6% ADN and 13.1% of MGN.

EXAMPLE 3

Hydrocyanation of 3-Pentenenitrile with Ligand/Ni $(COD)_2$: $SnCl_2$ Promoter

Performed the procedure of Example 2, but 170 mg of Ligand "A" (0.22 mmoles) and 14 mg of $SnCl_2$ (0.074 mmoles) as promoter were used. GC analysis indicated area % of 16.0% ADN and 3.9% of MGN.

EXAMPLE 4

Hydrocyanations of 3-Pentenenitrile with Ligand/Ni $(COD)_2$: $BPh_3$ Promoter

In a manner similar to Example 2, except using 170 mg of Ligand "A" (0.22 mmoles) and 15 mg (0.062 mmoles) of $BPh_3$ as promoter, hydrocyanation was carried out at 5 cc/min $N_2$ at 40° C. After 3 hours, GC analysis indicated area % of 5.3% ADN and 0.39% of MGN.

Similarly, the experiment was repeated as above with 340 mg (0.43 mmoles) of Ligand "A", 40 mg of $Ni(COD)_2$ (0.14 mmoles) and 15 mg (0.062 mmoles) of $BPh_3$. Hydrocyanation was carried out at 3 cc/min $N_2$ at 40° C. After 2 hours, GC analysis indicated area % of 39.1 ADN and 2.1% of MGN.

EXAMPLE 5

Hydrocyanation of 3-Pentenenitrile Using Ligand/ $Ni(COD)_2$: $Ph_3SnOTf$ Promoter Performed the procedure of Example 2 using 170 mg (0.22 mmoles) of Ligand "A" and 20 mg (0.073 mmoles) of $Ni(COD)_2$ with 10 mg (0.02 mmoles) of $Ph_3SnOTf$. Hydrocyanation was carried out at 12 cc/min $N_2$ at 50° C. for 5 hours. GC analysis indicated area % of 47.9% ADN and 2.0% of MGN.

EXAMPLE 6

Preparation of (COD)NiL

After removing the solvent from a THF solution of Ligand "A" with $Ni(COD)_2$, $^{31}P$ NMR in $C_6D_6$ consisted of two singlets at 178.9 and 146.6 ppm. The resonance at 146.6 ppm corresponded to free Ligand "A". The compound with resonance at 178.9 ppm was determined to be (COD)NiL. A THF solution containing 50 mg (0.18 mmoles) of $Ni(COD)_2$ and 215 mg of ligand (0.27 mmoles) was stirred overnight. A white precipitate formed which was filtered to give 0.206 g of (COD)NiL. $^{31}P$ NMR in $C_6D_6$: 178.9 ppm. $^1H$ NMR in $C_6D_6$: 7.7 (d, 2H), 7.2 (m, 8H), 7.0 (m, 6H), 6.9 (d, 2H), 6.6 (d, 2H), 4.8 (m, 2H), 4.2 (m, 2H), 2.9 (s, 6H), 2.0 (m)+1.7 (s)+1.4 (m) (total area, 26H).

EXAMPLE 7

Preparation of Nickel Catalyst from $Ni(acac)_2$/ $AlEt_3$ and Ligand

A mixture containing 0.219 g (0.85 mmoles) of $Ni(acac)_2$ (acac=acetylacetonate) and 1.004 g (1.28 mmoles) of Ligand "A" in 12 mL of toluene was cooled to 0° C. and 1.3 mL of $AlEt_3$ (25% solution in toluene, 2.5 mmoles) was added. The mixture was warmed to room temperature and then heated to 65° C. for 15 minutes. The mixture was stirred overnight, concentrated by vacuum evaporation and hexane added to yield 1.00 g of yellow solid. $^{31}P$ NMR in $C_6D_6$: singlets at 169.8 and 162.8 ppm. $^{31}P$ NMR indicates a 1:1 mixture of $NiL_2$ and NiL(ethylene).

EXAMPLE 8

Preparation of Nickel Catalyst from $Ni(acac)_2$/ $AlEt_3$ and Ligand

The procedure of Example 7 was repeated using 2.193 g (8.54 mmoles) of $Ni(acac)_2$, 10.073 g (12.8 mmoles) of Ligand "A" and 12.3 mL (23.4 mmoles) of $AlEt_3$. Hexane addition to the concentrated reaction mixture yielded 5.866 g of gray solid. This material was not soluble in $C_6D_6$. $^{31}P$ NMR in THF-$d_8$ consisted of a singlet at 166.9 ppm. This material was designated sample "8A". The filtrate was concentrated again and hexane added to precipitate out 1.916 g of yellow solid. $^{31}P$ NMR in $C_6D_6$: 169.7 ppm. This material was designated sample "8B".

EXAMPLE 9

Preparation of Nickel Catalyst from $Ni(acac)_2$/ $AlEt_3$ and Ligand

The procedure of Example 8 was repeated using 1.102 g (4.29 mmoles) $Ni(acac)_2$, 5.062 g (6.43 mmoles) of Ligand "A", and 6.5 mL (12.4 mmoles) of $AlEt_3$. The mixture was not heated to 65° C. but stirred at room temperature overnight. After concentrating and adding hexane, 4.340 g of yellow solid was isolated. $^{31}P$ NMR in $C_6D_6$ matched that of Example 7 but also showed a small peak at 159.4 ppm. NMR indicated a 2:1 ratio of LNi(ethylene): $L_2Ni$.

EXAMPLE 10

Hydrocyanation of 3-Pentenenitrile Using Catalyst Prepared from Example 7

To 0.175 g (0.12 mmoles of nickel) of sample from Example 7 and 0.190 g (0.24 mmoles) of Ligand "A" were added 5 mL of 3PN and 20 mg (0.04 mmoles) of $Ph_3SnOTf$. The mixture was treated with HCN at 12 cc/min of $N_2$ at 50° C. After heating at 50° C. for 2.5 hr, the mixture was heated at 70° C. for 0.5 hour. GC analysis using indicated area % of 85.7% ADN and 4.0% of MGN.

EXAMPLE 11

Hydrocyanation of 3-Pentenenitrile Using Catalyst Prepared from Example 8 (8A)

0.175 g (0.11 mmoles of nickel) of sample "8A", and 0.190 g (0.24 moles) of Ligand "A" were added to 5 mL of 3-pentenenitrile and 20 mg (0.04 moles) of $Ph_3SnOTf$. The mixture was treated with HCN at 12 cc/min $N_2$ at 50° C. After 2.5 hour, GC analysis indicated area % of 64.5% of ADN and 2.3% of MGN.

EXAMPLE 12

Hydrocyanation of 3-Pentenenitrile Using Catalyst Prepared from Example 8 (8B)

175 mg (0.11 moles of nickel) of sample "8B" and 190 mg (0.24 mmoles) of Ligand "A" in 5 mL of 3PN was added to 20 mg (0.04 mmoles) of $Ph_3SnOTf$. The mixture was treated with HCN at 12 cc/min $N_2$ at 50° C. After 3 hours, GC analysis indicated area % of 21.9% ADN and 2.5% MGN.

EXAMPLE 13

Hydrocyanation of 3-Pentenenitrile Using Catalyst Prepared from Example 9

To 0.175 g (0.15 moles of nickel) of the product from Example 9 and 0.190 g (0.24 moles) of Ligand "A" were added 5 mL of 3-pentenenitrile and 20 mg (0.04 moles) of $Ph_3SnOTf$. 500 mg of HCN in 2 mL of toluene was added and the mixture heated to 50° C. After 1 hour, GC analysis indicated mole % of 37.4% ADN and 2.2% MGN. Another 500 mg of HCN in 2 mL of toluene was added and the mixture stirred at 70° C. overnight. GC analysis indicated mole % of 64.7% ADN and 3.7% MGN.

EXAMPLE 14

Hydrocyanation of 3-Pentenenitrile Without Promoter 170 mg (0.22 moles) of Ligand "A" and 20 mg (0.073 moles) of $Ni(COD)_2$ were dissolved in 5 mL of THF. The solvent was removed by vacuum evaporation. To the mixture was added 5 mL of 3-pentenenitrile. The mixture was hydrocyanated at 12 cc/min $N_2$ at 50° C. After two hours, GC analysis indicated area % of 1.5% ADN, 0.1% MGN and 0.02% of 2-ethylsuccinonitrile (ESN).

EXAMPLE 15

Hydrocyanation of Methyl-3-Pentenoate with $Ph_3SnOTf$ Promoter 170 mg (0.10 mmoles) of LNi (ethylene) and $NiL_2$ in a mole ratio of 1:1.5 and 190 mg (0.24 moles) of Ligand "A"

were added 5 mL of methyl-3-pentenoate. To this mixture was added 20 mg (0.04 mmoles) of $Ph_3SnOTf$. The mixture was hydrocyanated at 12 cc/min $N_2$ at 50° C. for 2 hours and at 70° C. for 2 hours. After this time, GC analysis indicated area % of 0.8% 3-cyanomethylvalerate; 3.5% of 4-cyanomethylvalerate and 59.9% of 5-cyanomethylvalerate.

EXAMPLE 16

Hydrocyanation of 1-octene with Zinc Chloride Promoter

To 5 mL of THF was added 340 mg (0.43 moles) of Ligand "A" and 40 mg (0.14 mmoles) of $Ni(COD)_2$. The solvent was removed and 3 mL of toluene, 2 mL of 1-octene and 10 mg (0.073 mmoles) of $ZnCl_2$ were added. The mixture was hydrocyanated at 12 cc/min $N_2$ at 60° C. After 2 hours, GC analysis indicated area % of 16% n-octylcyanide.

EXAMPLE 17

Hydrocyanation of Perfluorobutyulethylene

To 5 mL of THF was added 340 mg (0.43 moles) of Ligand "A" and 40 mg (0.14 mmoles) of $Ni(COD)_2$. The solvent was removed and 5 mL of toluene, 2 mL of perfluorobutylethylene and 10 mg (0.073 mmoles) of $ZnCl_2$ were added. The mixture was hydrocyanated at 12 cc/min $N_2$ at 40° C. After 0.5 hours, GC analysis indicated that all of the olefin has been converted to perfluorobutyl-$CH_2CH_2$—CN.

COMPARATIVE EXAMPLE 18

Hydrocyanation Using Bidentate Ligand "B"

Ligand "B"

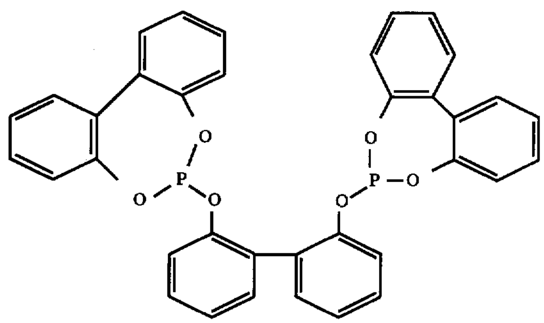

75 mg (0.12 mmoles) of the above Ligand "B" and 20 mg (0.07 mmoles) of $Ni(COD)_2$ were dissolved in 5 mL of THF and the solvent was removed. 5 mL of 3-pentenenitrile and 10 mg (0.073 mmoles) of $ZnCl_2$ were added. The mixture was treated with HCN at 40° C. at 30 cc/min $N_2$. No conversion to adiponitrile was observed after 1.5 hours. The procedure was repeated but with 0.150 g (0.24 mmoles) of the above Ligand "B" and HCN at 30 cc/min $N_2$ at 50° C. for 15 min., 60° C. for 15 min and 70° C. for 15 min. After this time, no adiponitrile was observed.

COMPARATIVE EXAMPLE 19

Hydrocyanation Using Ligand "C"

Ligand "C"

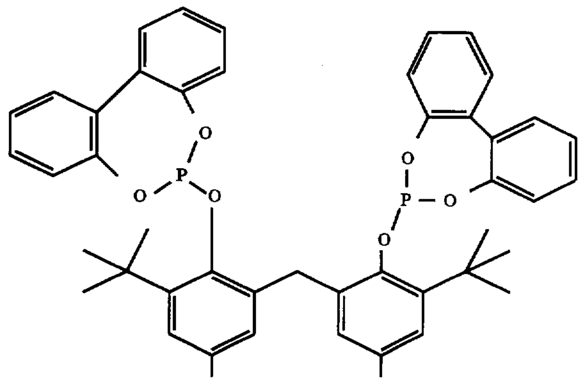

To 160 mg (0.21 mmoles) of the above Ligand "C" and 20 mg (0.07 mmoles) of $Ni(COD)_2$ was added 5 mL THF. The solvent was removed and 5 mL of 3-pentenenitrile and 10 mg (0.073 mmoles) of $ZnCl_2$ were added. Hydrocyanation was done at 30 cc/min $N_2$ at 50° C. for 15 min, 60° C. for 15 min and 70° C. for 15 min. No adiponitrile product was generated.

EXAMPLE 20

Hydrocyanation of 2-Pentenenitrile

A mixture of $NiL_2$ (L=Ligand "A") (0.100 g; 0.06 mmol), $Ph_3Sn(O_3SCF_3)$ (0.030 g; 0.06 mmol), cis-2-pentenenitrile (0.017 g; 0.21 mmol) in benzene (1.30 mL) and acetonitrile (0.50 mL) was heated (71° C.) with stirring under nitrogen atmosphere in a septum capped glass vial. HCN (50 uL of 2.55M HCN in benzene; 0.0034 g HCN; 0.13 mmol) was injected into the mixture and aliquots removed periodically and analyzed by GC. After 1 hr, the mixture contained 2-pentenenitrile (0.082 mmol), adiponitrile (0.110 mmol), 2-methylglutaronitrile (0.006 mmol), 2-ethylsuccinonitrile (0.002 mmol), and valeronitrile (0.007 mmol).

EXAMPLE 21

Hydrocyanation Using Ligand "D"

Ligand "D"

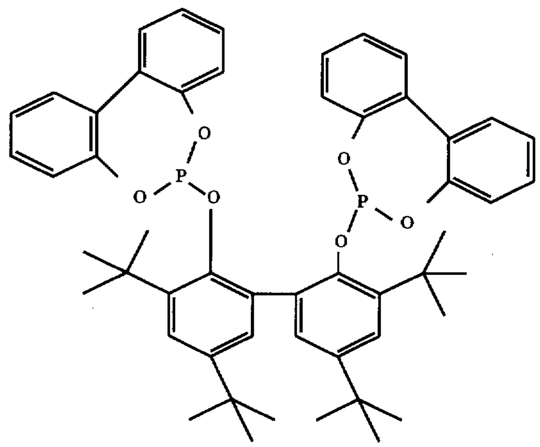

This ligand, D, was prepared similarly to Ligand "A" starting with the oxidation of 2,4-di-t-butylphenol to give the biphenol followed by the reaction with 1,1'biphenyl-2, 2'-diyl phosphorocholoridite. n-BuLi was used as the base instead of $NEt_3$. 369 mg of Ligand "D" and 40 mg of $Ni(COD)_2$ were dissolved in 5 mL of THF and the solvent removed. 5 mL of 3PN and 20 mg of $ZnCl_2$ were added. The mixture was treated with HCN at 80° C. at 12 cc/min $N_2$. After 1.5 hr, 31.1% of ADN, 7.9% of MGN and 0.8% of ESN were obtained as determined by GC analysis.

EXAMPLE 22

Hydrocyanation Using Ligand "E"

Ligand "E"

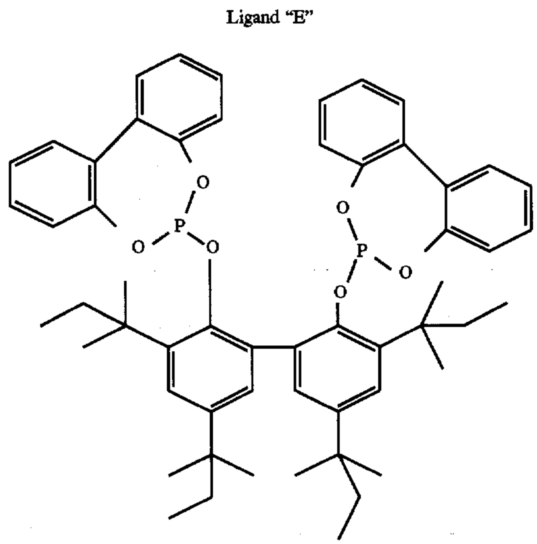

This ligand, E, was prepared similarly to Ligand "A" starting with the air oxidation of 2,4-di-t-pentylphenol to give the biphenol followed by treatment with 1,1'biphenyl-2,2'-diyl phosphorochloridite. n-BuLi was used as the base instead of $NEt_3$. $^{31}P$ NMR in $C_6D_6$: 145.1 ppm. 380 mg of Ligand "E" and 40 mg of $Ni(COD)_2$ were dissolved in 5 mL of THF and the solvent removed. 5 mL of 3PN and 20 mg of $ZnCl_2$ were added. The mixture was treated with HCN at 50°, 60°, 70°, 80°, and 100° C. for 15 minutes each at 12 cc/min $N_2$. After heating at 100° C., 36.8% of ADN, 8.5% of MGN and 0.9% of ESN were obtained as determined by GC analysis.

EXAMPLES 23 TO 57

Use of Other Lewis Acid Promoters in the Hydrocyanation of 3-Pentenenitrile [L=Ligand "A"]

A mixture $NiL_2$ (0.230 g; 0.14 mmol) and L (0.110 g; 0.14 mmol), 3-pentenenitrile (5.0 mL; 52 mmol), and a Lewis acid promoter (0.14 mmol) (indicated in the Table) was heated at 70° C. and treated with HCN via vapor transfer as described above (N₂ flow=12 cc/min) for 2 hours. The results in terms of percent conversion and percent selectivity are presented in the Table below. Conversion and selectivity are defined as follows:

Conversion=100×(ADN+MGN+ENS)/(initial 3PN)

Selectivity=100×ADN/(ADN+MGN+ESN)

where ADN is adiponitrile, MGN is 2-methylglutaronitrile, ESN is 2-ethylsuccinonitrile, and 3PN is 3-pentenenitrile.

TABLE

| Ex. | Promoter | Conversion % | Selectivity % |
|---|---|---|---|
| 23 | $ZnBr_2$ | 26 | 83 |
| 24 | $ZnI_2$ | 59 | 82 |
| 25 | $ZnCl_2$ | 64 | 76 |
| 26 | $ZnSO_4$ | 31 | 79 |
| 27 | $CuCl_2$ | 7 | 89 |
| 28 | CuCl | 13 | 80 |
| 29 | $Cu(O_3SCF_3)_2$ | 4 | 95 |
| 30 | $CoCl_2$ | 28 | 74 |
| 31 | $CoI_2$ | 28 | 79 |
| 32 | $FeI_2$ | 25 | 79 |
| 33 | $FeCl_3$ | 14 | 71 |
| 34 | $FeCl_2(THF)_2$* | 52 | 75 |
| 35 | $TiCl_4(THF)_2$* | 12 | 87 |
| 36 | $TiCl_4$ | 25 | 80 |
| 37 | $TiCl_3$ | 24 | 85 |
| 38 | $MnCl_2$ | 41 | 79 |
| 39 | $ScCl_3$ | 13 | 88 |
| 40 | $AlCl_3$ | 15 | 85 |
| 41 | $(C_8H_{17})AlCl_2$ | 26 | 82 |
| 42 | $(i\text{-}C_4H_9)_2AlCl$ | 3 | 83 |
| 43 | $Ph_2AlCl$ | 13 | 81 |
| 44 | $ReCl_5$ | 22 | 97 |
| 45 | $ZrCl_4$ | 25 | 87 |
| 46 | $NbCl_5$ | 2 | 85 |
| 47 | $VCl_3$ | 7 | 85 |
| 48 | $CrCl_2$ | 1 | 80 |
| 49 | $MoCl_5$ | 3 | 78 |
| 50 | $YCl_3$ | 48 | 88 |
| 51 | $CdCl_2$ | 60 | 80 |
| 52 | $LaCl_3$ | 31 | 87 |
| 53 | $Er(O_3SCF_3)_3$ | 34 | 90 |
| 54 | $Yb(O_2CCF_3)_3$ | 36 | 84 |
| 55 | $SmCl_3$ | 40 | 83 |
| 56 | $BPh_3$ | 40 | 95 |
| 57 | $TaCl_5$ | 4 | 85 |

*Tetrahydrofuran

EXAMPLE 58

Preparation of the Ligand of Formula II Where $R^6$ and $R^7$ are t-butyl and $R^8$ is $OCH_3$ (Ligand "F")

Ligand "F"

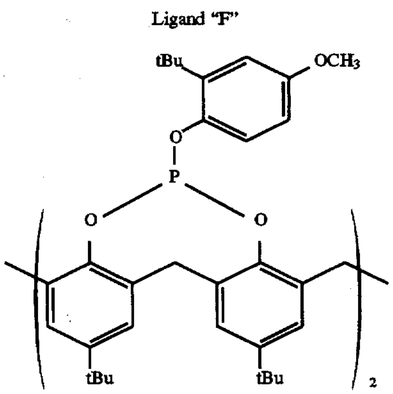

To 1.44 g of the dichlorodite derived from $PCl_3$ and 2-t-butyl-4-methoxyphenol in 20 mL of toluene was added 1.66 g of 4-t-butylcalix[4]arene and 1.3 g of triethyl amine in 20 mL of toluene. The mixture was stirred overnight and refluxed for one hour. The cooled mixture was filtered through celite, washed with toluene and solvent removed to give 2.04 g of the desired product as a white solid. $^{31}P$ {1H} (121.4 MHz, $C_6D_6$): 116.06 ppm.

EXAMPLE 59

Hydrocyanation Using Ligand "F"

464 mg of Ligand "F" and 0.040 g of $Ni(COD)_2$ were dissolved in 5 mL of tetrahydrofuran. The solvent was removed and 20 mg of $ZnCl_2$ and 5 mL of 3-pentenenitrile (3-PN) were added. The mixture was treated with HCN with a nitrogen flow rate of 12 cc/min. The oil bath was initially at 50° C. After 15 minutes, the temperature controller was set at 60° C. After 15 minute intervals, the temperature controller was set at 70°, 80°, and 100° C. After 15 minutes at the last temperature setting, GC analysis indicated 19.0% adiponitrile (ADN), 6.3% 2-methylglutaronitrile (MGN) and 3.8% 2-ethylsuccinonitrile (ESN).

EXAMPLE 60

Preparation of the Ligand of Formula II Where $R^6$ and $R^7$ are t-butyl and $R^8$ is H (Ligand "G")

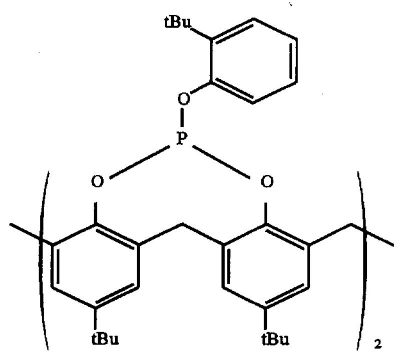

To 1.22 g of dichlorodite derived from $PCl_3$ and 2-t-butylphenol in 20 mL of toluene was added 1.66 g of 4-t-butylcalix[4]arene and 1.3 g of triethylamine in 20 mL of toluene. The mixture was stirred overnight and refluxed for one hour. The cooled mixture was filtered through celite, washed with toluene and solvent removed to give 1.926 g of the desired product as a white solid. $^{31}P\{1H\}$(121.4 MHz, $C_6D_6$): 115.6 ppm.

EXAMPLE 61

Hydrocyanation Using Ligand "G"

342 mg of Ligand "G" and 0.040 g of $Ni(COD)_2$ were dissolved in 5 mL of tetrahydrofuran. The solvent was removed and 20 mg of $ZnCl_2$ and 5 mL of 3PN were added. The mixture was treated with HCN with a nitrogen flow rate of 12 cc/min. The oil bath was initially at 50° C. After 15 minutes, the temperature controller was set at 60° C. After 15 minute intervals, the temperature controller was set at 70°, 80°, and 100° C. After 15 minutes at the last temperature setting, GC analysis indicated 17.1% ADN, 6.4% MGN, and 5.9% ESN.

EXAMPLE 62

Preparation of the Ligand of Formula III Where $R^9$ is $OCH_3$ and $R^{10}$ are t-butyl (Ligand "H")

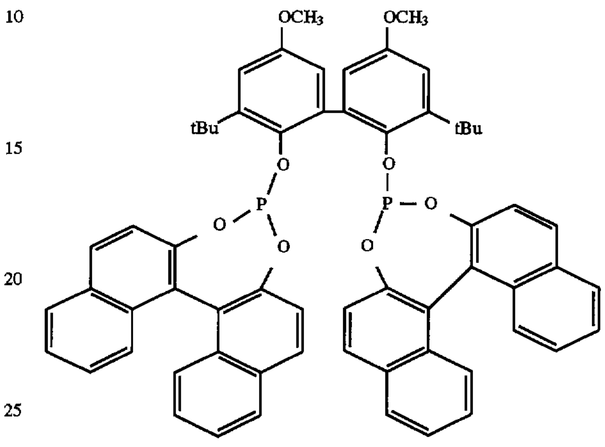

To 0.7 mL of $PCl_3$ in 15 mL of toluene at 0° C. was added 2.3 g of 1,1'-bi-2-naphthol and 4.1 mL of triethylamine in 20 mL of toluene. The mixture was stirred at room temperature. To 1.43 g of 2,2'-dihydroxy-3,3'-di-t-butyl-5,5'-dimethoxy-1,1'-biphenyl in 15 mL of toluene at −20° C. was added 4.5 mL of 1.77M n-butyl lithium in hexane. The mixture was stirred at room temperature for one hour and the above chlorodite solution was added. The mixture was stirred overnight and then filtered through celite, washed with toluene and solvent removed to give 4.044 g of the product as a light yellow solid. $^{31}P\{1H\}$(121.4 MHz, $C_6D_6$): 146.84, 146.74, 146.62, 146.20, 146.10, 145.76, 145.41, 145.00, and 144.89 ppm. FABMS: Found: M+H 987.10; Calculated for $C_{62}H_{52}O_8P_2$+H: 987.32.

EXAMPLE 63

Hydrocyanation Using Ligand "H"

445 mg of Ligand "H" and 0.040 g of $Ni(COD)_2$ were dissolved in 5 mL of tetrahydrofuran. The solvent was removed and 20 mg of $ZnCl_2$ and 5 mL of 3PN were added. The mixture was treated with HCN with a nitrogen flow rate of 12 cc/min. The temperature bath was initially at 50° C. After 15 minutes, the temperature controller was set at 60° C. After 15 minute intervals, the temperature controller was set at 70°, 80°, and 100° C. After 15 minutes at the last temperature setting, GC analysis indicated 37.1% ADN, 5.0% MGN, and 0.9% ESN.

EXAMPLE 64

Preparation of the Ligand of Formula IV Where $R^{14}$ is Triphenyl Silyl (Ligand "J")

Ligand "J"

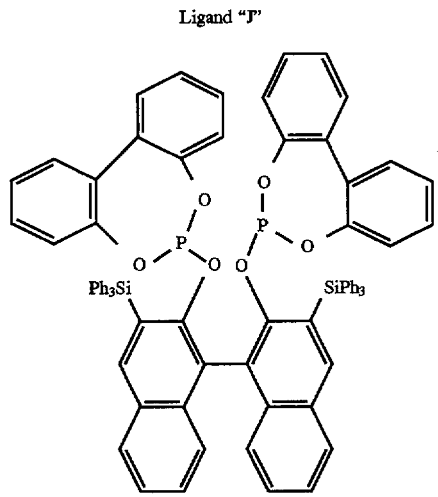

Chloridite (0.34 g/1.37 mmol) derived from 2,2'-biphenol and $PCl_3$ was dissolved in toluene (10 mL) and the solution was cooled to −40° C. 3,3'-Triphenylsilyl-1,1'-bi-2-naphthol (0.80 g/0.68 mmol) and triethylamine (0.5 mL) were dissolved in toluene (15 mL) and this solution was added dropwise to the cold solution. The mixture was stirred overnight at room temperature. The solids were filtered and the solvent was removed to give 0.65 g of a light yellow solid. $^{31}P$ NMR ($CDCl_3$): δ 146.23 (small peak), 136.37 (major peak) and 13 (small peak).

EXAMPLE 65

Hydrocyanation Using Ligand "J"

517 mg of Ligand "J", 0.020 g of $ZnCl_2$ and 0.040 g of $Ni(COD)_2$ were dissolved in 5 mL of 3PN. The mixture was treated with HCN with a nitrogen flow rate of 30 cc/min at 70° C. for one hour. GC analysis indicated 9.3% ADN, 0.6% MGN, and 0.1% ESN.

EXAMPLE 66

Preparation of the Ligand of Formula V Where $R^{12}$ is H and Each $R^{13}$ is $CH_3$ (Ligand "K")

Ligand "K"

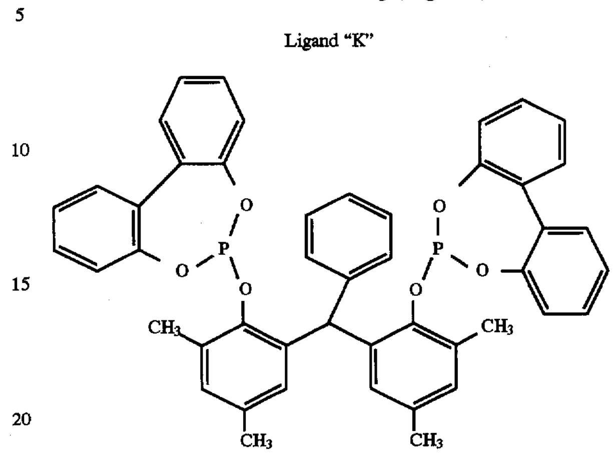

To 2.0 g of the chloridite derived from 2,2'-biphenol and $PCl_3$ in 20 mL of toluene was added 1.95 g of 2,2'-benzylidenebis(4,6-dimethylphenol) (prepared by the procedure of Yamada, F.; Nishiyama, T.; Yamamoto, M.; and Tanaka, K.; Bull. Chem. Soc. Jpn., 62, 3603 (1989)) and 2 g of triethylamine in 20 mL of toluene. The mixture was stirred overnight and refluxed for one hour. The cooled mixture was filtered through celite, washed with toluene and solvent removed to give 3.912 g of the desired product as a tan solid. $^{31}P$ ($^{1}H$) (121.4 MHz, $C_6D_6$): 148.00 ppm.

EXAMPLE 67

Hydrocyanation Using Ligand "K"

327 mg of Ligand "K" and 0.040 g of $Ni(COD)_2$ were dissolved in 5 mL of tetrahydrofuran. The solvent was removed and 20 mg of $ZnCl_2$ and 5 mL of 3PN were added. The mixture was treated with HCN with a nitrogen flow rate of 30 cc/min at 70° C. for one hour. GC analysis indicated 12.9% ADN, 42.% MGN, and 0.4% ESN.

COMPARATIVE EXAMPLE 68

Preparation of Ligand "L"

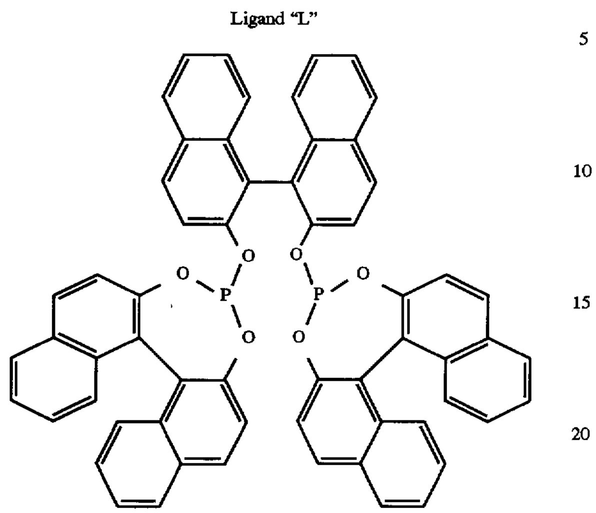

Ligand "L" was prepared according to the procedure described in Example 6 of WO 93/03839, with the exception that the weight of $PCl_3$ listed in the literature procedure did not correspond to the number of moles of $PCl_3$ needed, so the appropriate adjustment was made. Phosphorus trichloride (0.32 g; 2.3 mmol) was dissolved in toluene (10 mL) and the solution was cooled to 0° C. S-1-1'-bi-2-naphthol (1.0 g; 3.5 mmol) and to 0° C. S-1-1'-bi-2-naphthol (1.0 g; 3.5 mmol) and triethylamine (0.8 mL; 6.0 mmol) were dissolved in toluene (30 mL) and this solution was added dropwise to the $PCl_3$ solution. The mixture was then heated to reflux for 2 hours. The solids were filtered off and the solvent was removed to give 0.8 g of white solid. $^{31}P$ NMR ($CDCl_3$): δ 145.4.

COMPARATIVE EXAMPLE 69

Hydrocyanation Using Ligand "L"

384 mg of Ligand "L", 0.020 g of $ZnCl_2$ and 0.040 g of $Ni(COD)_2$ were dissolved in 5 mL of 3PN. The mixture was treated with HCN with a nitrogen flow rate of 30 cc/min at 70° C. for one hour. GC analysis indicated 1.8% ADN, 0.8% MGN, and 0.2% ESN.

COMPARATIVE EXAMPLE 70

Hydrocyanation Using Ligand "L"

3.84 mg of Ligand "L", 0.020 g of $ZnCl_2$ and 0.040 g of $Ni(COD)_2$ were dissolved in 5 mL of 3PN. The mixture was treated with HCN with a nitrogen flow rate of 30 cc/min at 70° C. for one hour. GC analysis indicated 3% ADN, 1.5% MGN, and 0.3% ESN.

COMPARATIVE EXAMPLE 71

Preparation of Ligand "M"

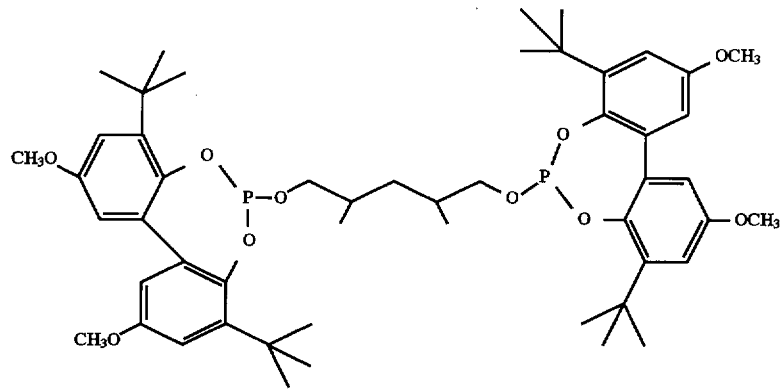

Ligand "M" was prepared according to the procedure described in Example 1 of WO 93/0383.9. Phosphorus trichloride (0.66 g; 4.8 mmol) was dissolved in toluene (15 mL) and cooled to 0° C. The 2,2'-dihydroxy-3,3'-di-t-butyl-5,5'-dimethoxy-1,1'-biphenyl (1.72 g; 4.8 mmol) and triethylamine (2.7 mL; 19.2 mmol) were dissolved in toluene (25 mL). This solution was added dropwise to the cold $PCl_3$ solution. After the addition was complete, the mixture was heated to reflux for 1.5 hrs. The mixture was then cooled to 0° C., and solid (2R,4R)-(−)-pentanediol (0.25 g; 2.4 mmol) was added. The mixture was again heated to reflux for 1.5 hrs., and then stirred overnight at room temperature. The solids were filtered, and the toluene was removed in vacuo. The resulting yellow solid was dissolved in hot $CH_3CN$ (approx. 10 mL) and stirred at room temperature. The resulting white solid was removed, washed with cold $CH_3CN$, and dried. 1.3 g of material was collected. $^{31}P$ NMR ($CDCl_3$): δ 146.2.

COMPARATIVE EXAMPLE 72

Hydrocyanation Using Ligand "M"

368 mg of Ligand "M", 0.020 g of $ZnCl_2$ and 0.040 g of $Ni(COD)_2$ were dissolved in 5 mL of 3PN. The mixture was treated with HCN with a nitrogen flow rate of 30 cc/min at 70° C. for one hour. GC analysis indicated 0.0% ADN, 0.2% MGN, and 0.0% ESN.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than the foregoing specification, as indicating the scope of the invention.

We claim:

1. A process for hydrocyanation, comprising reacting a nonconjugated acyclic aliphatic monoolefin, monoolefin conjugated to an ester group or monoolefin conjugated to a nitrile group with a source of HCN in the presence of a catalyst precursor composition comprising zero-valent nickel and a bidentate phosphite ligand of Formula I,

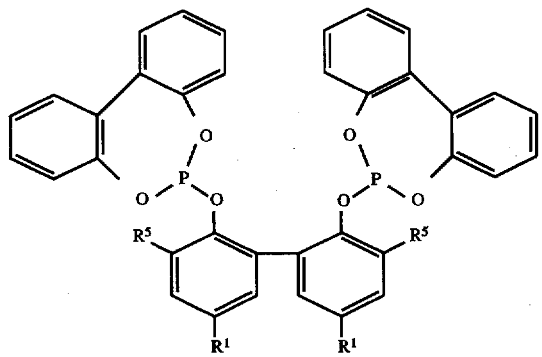

wherein each $R^1$ is independently a tertiary substituted hydrocarbon of up to 12 carbon atoms, or $OR^4$ wherein $R^4$ is $C_1$ to $C_{12}$ alkyl;

each $R^5$ is independently a tertiary substituted hydrocarbon of up to 12 carbon atoms;

and wherein said reaction is carried out to produce a terminal organonitrile.

2. The process of claim 1 wherein the reaction is carried out in the presence of a Lewis acid promoter.

3. The process of claims 1 or 2 wherein the nonconjugated acyclic aliphatic monoolefin, monoolefin conjugated to an ester group or monoolefin conjugated to a nitrile group are compounds of Formula VI

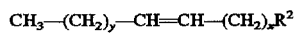

$$CH_3-(CH_2)_y-CH=CH-(CH_2)_xR^2 \quad \text{VI}$$

wherein $R^2$ is H, CN, $CO_2R^3$, or perfluoroalkyl;

y is 0 to 12;

x is 0 to 12; and $R^3$ is alkyl;

and the terminal organonitrile product is a compound of Formula VII $$NC-(CH_2)_{y+x+3}-R^2 \quad \text{VII}$$

wherein $R^2$, y and x are as defined above.

4. The process of claims 1 or 2 wherein the nonconjugated acyclic aliphatic monoolefin, monoolefin conjugated to an ester group or monoolefin conjugated to a nitrile group are compounds of Formula VIII

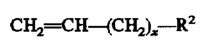

$$CH_2=CH-(CH_2)_x-R^2 \quad \text{VIII}$$

wherein $R^2$ is H, CN, $CO_2R^3$, or perfluoroalkyl;

x is 0 to 12; and $R^3$ is alkyl, and the terminal organonitrile product is a compound of Formula IX $$NC-(CH_2)_{x+2}-R^2 \quad \text{IX}$$

wherein $R^2$ and x are as defined above.

5. The process of claims 1 or 2 wherein each $R^1$ is $OR^4$ wherein $R^4$ is independently methyl, ethyl, isopropyl, or t-butyl.

6. The process of claim 5 wherein each $R^1$ is $OR^4$ wherein $R^4$ is methyl.

7. The process of claims 1 or 2 wherein the nonconjugated acyclic aliphatic monoolefin, monoolefin conjugated to an ester group or monoolefin conjugated to a nitrile group is 2-pentenenitrile, 3-pentenenitrile, 4-pentenenitrile, alkyl 2-penteneoate, alkyl 3-penteneoate, alkyl 4-penteneoate, or a compound $C_xF_{2x+1}CH=CH_2$ wherein x is 1 to 12.

8. The process of claims 1 or 2 wherein the terminal organonitrile is adiponitrile, alkyl 5-cyanovalerate, 3-(perfluoroalkyl)propionitrile, or a compound $C_xF_{2x+1}CH_2CH_2CN$ wherein x is 1 to 12.

9. The process of claim 2 wherein the Lewis acid promoter is an inorganic or organometallic compound in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin.

10. The process of claim 9 wherein the Lewis acid promoter is $ZnCl_2$, $CdCl_2$, $B(C_6H_5)_3$, or $(C_6H_5)_3SnX$ wherein X is $CF_3SO_3$, $CH_3C_6H_5SO_3$ or $(C_6H_5)_3BCN$.

11. The process of claims 1 or 2 wherein the reaction is carried out at a temperature of from 0° to 150° C. and at atmospheric pressure.

12. The process of claims 1 or 2 wherein each $R^1$ is $OR^4$ wherein each $R^4$ is methyl, and the monoolefin is 3-pentenenitrile.

13. The process of claims 1 or 2 wherein each $R^1$ is $OR^4$, wherein each $R^4$ is methyl, and the monoolefin is 2-pentenenitrile.

14. A catalyst precursor composition comprising zero-valent nickel and a bidentate phosphite ligand of Formula I

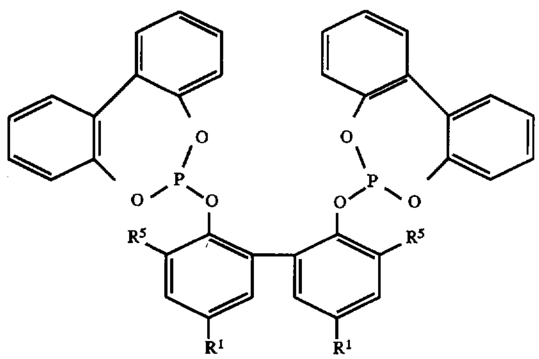

wherein each $R^1$ is independently a tertiary substituted hydrocarbon of up to 12 carbon atoms, or $OR^4$ wherein $R^4$ is $C_1$ to $C_{12}$ alkyl; and each $R^5$ is independently a tertiary substituted hydrocarbon of up to 12 carbon atoms.

15. The catalyst precursor composition of claim 14 further comprising a Lewis acid promoter.

16. The composition of claims 14 or 15 wherein each $R^1$ is $OR^4$ wherein each $R^4$ is alkyl.

17. The composition of claim 16 wherein each $R^1$ is $OR^4$ wherein each $R^4$ is methyl.

18. The composition of claims 14 or 15 wherein each $R^5$ is a tertiary hydrocarbon containing 4 carbon atoms.

* * * * *